US006352682B2

(12) United States Patent
Leavitt et al.

(10) Patent No.: US 6,352,682 B2
(45) Date of Patent: *Mar. 5, 2002

(54) POLYMERIC DELIVERY OF RADIONUCLIDES AND RADIOPHARMACEUTICALS

(75) Inventors: Richard D. Leavitt, Woodside, CA (US); Luis Z. Avila, Arlington, MA (US)

(73) Assignee: Focal, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/968,463

(22) Filed: Oct. 2, 1997

Related U.S. Application Data

(63) Continuation of application No. 08/613,904, filed on Mar. 11, 1996, now abandoned.

(51) Int. Cl.$^7$ ............................. A61K 51/00; A61N 5/00

(52) U.S. Cl. .................. 424/1.25; 424/1.29; 424/1.33; 600/3; 600/4

(58) Field of Search ............................... 424/1.25, 1.29, 424/1.33, 1.11; 600/1, 3, 4, 7, 8; 524/916; 252/625, 634

(56) References Cited

U.S. PATENT DOCUMENTS

| | | | |
|---|---|---|---|
| 1,645,599 A | | 10/1927 | Jones |
| 4,115,540 A | | 9/1978 | Digenis et al. |
| 4,268,495 A | * | 5/1981 | Muxfeldt et al. .......... 424/1.11 |
| 4,706,652 A | | 11/1987 | Horowitz |
| 5,084,002 A | | 1/1992 | Liprie |
| 5,102,666 A | | 4/1992 | Acharyg |
| 5,256,765 A | | 10/1993 | Leong |
| 5,410,016 A | | 4/1995 | Hubbell et al. |
| 5,493,007 A | | 2/1996 | Burnier et al. |
| 5,498,227 A | | 3/1996 | Mawad |
| 5,503,614 A | | 4/1996 | Liprie |
| 5,514,379 A | | 5/1996 | Weissleder et al. |
| 5,527,864 A | | 6/1996 | Suggs et al. |
| 5,575,749 A | | 11/1996 | Liprie |
| 5,575,815 A | | 11/1996 | Slepian et al. |
| 5,594,136 A | | 1/1997 | Sessler et al. |
| 5,611,767 A | | 3/1997 | Williams |
| 5,616,114 A | | 4/1997 | Thornton et al. |
| 5,618,266 A | | 4/1997 | Liprie |
| 5,643,171 A | | 7/1997 | Bradshaw et al. |
| 5,762,903 A | * | 6/1998 | Park et al. .................. 424/1.29 |
| 5,844,017 A | | 12/1998 | Jamiolowski et al. |
| 5,859,150 A | | 1/1999 | Jamiolowski et al. |
| 5,873,811 A | | 2/1999 | Wang et al. |

FOREIGN PATENT DOCUMENTS

| | | |
|---|---|---|
| EP | 0 433 011 A1 | 6/1991 |
| EP | 0 539 165 A1 | 4/1993 |
| EP | 0 593 136 A1 | 4/1994 |
| WO | WO 87/06241 | 10/1987 |
| WO | WO 96/03112 A1 | 2/1996 |
| WO | WO 96/03112 | 2/1996 |
| WO | WO 96/00588 | 4/1996 |

OTHER PUBLICATIONS

Medical Industry Today, Abstract No. 10259606, "IsoStent Completes First Human Implants of Stents," (Oct. 25, 1996).
Medical Industry Today, Abstract No. 11059608, "Novoste Trial Enrollment Completer, Poised to Begin Trials," (Nov. 5, 1996).
Medical Industry Today, Abstract No. 02209704 "Radiosotope Stent In Test to Treat Cardiovascular Disease," (Feb. 20, 1997).
Medical Industry Today, Abstract No. 02259706, "Medtronic Invests In On-Demand Blood Radiation Technology," (Feb. 25, 1997).
Medical Industry Today, Abstract No. 05059709, "Oncoath Cash Unfusion Advances Cancer Treatment Systems," (May 5, 1997).
* Medline Abstracts No. 90335606, Ball et al., "Silicone implant to prevent visceral damage during adjuvant radiotherapy for retroperitoneal sarcoma," *Brit. J. Radiology* 63(749):346–348 (1990).
* Medline Abstract No. 96033224, Durrani et al., "Precorneal clearance of mucoadhesive microspheres from the rabbit eye," *J. Pharmacy and Pharmacology*, 47(7):581–584 (1995).
Ning, et al., "Intratumoral radioimmunotherapy of a human colon cancer xenograft using a substained release," *Radiother. Oncol.* 39(2):179–189 (1996).
Weshler, et al., "Prevention of neointimal formation in de-endothilialized rat aorta" Abstract —*Proc. 21st Ann. Meeting, European Soc. Radiation Biol.* (1988).
Ball, et al., "Silicone implant to prevent visceral damage during adjuvant radiotherapy for retroperitoneal sarcoma," *Brit. J. Radiology* 63(749):346–348 (1990).
Böttcher, et al., "Endovascular irradiation—A new method to avoid recurrent stenosis after stent implantation in peripheral arteries: Technique and preliminary results," *Int. J. Radiation Oncology Biol. Phys.* 29(1):183–186 (1994).
Chemical Abstract 109:125450 Furukawa et al., *Jpn. Kokai Tokkyo Koho*, JP 62254773 A2, Abstract, 1987.
Chemical Abstracts No. 125(9):109075, Ning et al., "Intratumoral radioimmunotherapy of a human colon cancer xenograft using a sustained–release gel," *Radiother. Oncol.* 39(2):1790189 (1996).

(List continued on next page.)

Primary Examiner—Michael G. Hartley
(74) Attorney, Agent, or Firm—Holland & Knight LLP

(57) ABSTRACT

Locally deposited polymer depots are used as a vehicle for the immobilization and local delivery of a radionuclide or radiopharmaceutical. Radionuclides are incorporated in their elemental forms, as inorganic compounds, or are attached to a larger molecule or incorporated into the polymer, by physical or chemical methods. Ancillary structure may be employed to control the rate of release. Standard radionuclides which have been used for local radiotherapy may be used, such as radionuclides of iodine, iridium, radium, cesium, yttrium or other elements.

15 Claims, No Drawings

OTHER PUBLICATIONS

Durrani, et al., "Precorneal Clearance of Mucoadhesive Microspheres from the Rabbit Eye," *J. Pharm. Pharmacol.* 47(7):581–584 (1995).

Friedman, et al., "The Antiatherogenic Effect of Iridium$^{192}$ upon the Cholesterol–fed Rabbit," *J. Clin. Invest.*, 43(2):185–192 (1964).

Friedman, et al., "Aortic Atherosclerosis Intensification in Rabbits by Prior Endothelial Denudation," *Arch. Path.* 79:345–356 (1965).

Friedman, et al., "Effect of Iridium 192 Radiation on Thromboatherosclerotic Plaque in the Rabbit Aorta," *Arch. Path.*, 80:285–290 (1965).

Furukawa, et al., "Catheter for in situ cavity irradiation for radio therapy," CA vol. 109(15) Abstract No. 125450 (1988).

Laakso, et al., "Biodegradable Microspheres X: Some Properties of Polyacryl Starch Microparticles Prepared From Acrylic Acid Esterified Starch," *J. Pharm. Sci.*, 76(12):935–939 (1987).

Medical Industry Today, Abstract No. 08219606, "Novoste, Emory Univ. Settle Patent Flap," (Aug. 21, 1996).

Freeman, et al., "Targeted drug delivery," *Cancer* 58:573–583 (1986).

Kalmykova, et al., "Changes in the entropy of heart mass in dogs during inhalation of transuranic radionuclides," *Meditsinskaia Radiologiia* 36(5):27–30 (1991).

\* cited by examiner

POLYMERIC DELIVERY OF RADIONUCLIDES AND RADIOPHARMACEUTICALS

This is a continuation of Ser. No. 08/613,904, filed on Mar. 11, 1996, by Richard D. Leavitt and Luis Z. Avila for "Polymeric Delivery of Radionuclides and Radiopharmaceuticals", now abandoned.

BACKGROUND OF THE INVENTION

This relates to an improved method of local radiotherapy, and devices and compositions for accomplishing local radiotherapy.

Radiation has been used for cancer therapy and to control local healing in areas as diverse as preventing excessive scar formation or reducing lymphoid infiltration and proliferation. More recently, radiation has been used to inhibit restenosis following coronary artery or peripheral artery angioplasty. Interstitial radiation by use of radioactivity incorporated into intravascular stents, delivery of radiation dose by use of catheters containing radioactive sources, and external beam radiotherapy have been used.

There are disadvantages to each of these approaches. When radiation is delivered by an extracorporeal beam, the usual problems of limiting the exposure only to those tissues intended to be affected are encountered. Moreover, doses must often be subdivided, requiring more than one visit to the hospital by the patient. If radiation is to be delivered by a catheter or other temporarily-installed medical device, then the rate of delivery of radiation from the device must be high. The active source will normally require careful shielding, even if relatively "soft" radiation, such as beta rays, is used. If administered in the same operation as balloon angioplasty or cardiac bypass, extra complications of an already complex and risky procedure are magnified. Delivery of radiation on a permanently implanted device, or a biodegradable device that necessarily is eroded over a long period of time because it also provides structural support, severely limits the choice of radioisotope because of the need to limit the total delivered dose to the tissue, while simultaneously providing sufficient initial dose to achieve the required effect. Moreover, repetition of the administration, if required, is not readily achieved.

The object of this invention is to provide an improved method for localized radiotherapy for the cure or alleviation of medical conditions.

SUMMARY OF THE INVENTION

Locally deposited biodegradable polymer depots are used as a vehicle for the immobilization and local delivery of a radionuclide or radiopharmaceutical. Radionuclides are incorporated in their elemental forms, as inorganic compounds, or are attached to a larger molecule or incorporated into the polymer, by physical or chemical methods. Ancillary structures may be employed to control, the rate of release. The depot is preferably made of a biodegradable material which is selected to degrade at a known rate under conditions encountered at the site of application. The depot is preferably fluent, or capable of being made fluent, so that it may be deposited at a site in a conforming manner by minimally invasive means. Examples of such materials are melted polymers which re-solidify at body temperature, and polymerizable materials which are polymerized at the site of deposition. The depot optionally is provided with means for controlling the rate of release of the radioactive compound. These means may include microparticles in which the radioactive compound is incorporated.

The use of the polymeric depots provides a way of immobilizing the source of energy from a radioactive source at a remote site within the body, which can be accessible by a less invasive surgical procedure, such as by catheter or laparoscopy. The duration and total dose of radiation can be controlled by a combination of choice of the radionuclide, control of the rate of degradation of the polymer, and control of the rate of release of the radionuclide from the depot. Following polymer degradation and/or release of the radionuclide, excretion from the body in urine and stool can be favored by administering pharmaceutical agents which favor excretion. For example, in the case of iodine radionuclides, excretion can be favored by blocking thyroid uptake of radioactive iodine or iodinated compounds by systemic administration of non-radioactive iodine compounds, such as sodium iodide or Lugol's solution.

DETAILED DESCRIPTION OF THE INVENTION

The polymeric depots provide a method of delivery of a radioactive agent to a local site of disease for treatment, such as for prevention of restenosis following angioplasty. The method has advantages over other methods of local radiation delivery in all applications, because the duration and intensity of the exposure can be altered by choosing radionuclides of differing physical half-life, and the biological half-life can be controlled by accelerating or retarding the rate of release of the radionuclide from the polymeric matrix. This provides a way to control local dosage of radiation without the need for physical removal of the implanted radionuclide. Radioactivity can thus be applied at any site in the body that is accessible by a less invasive procedure or catheter, for example, to a coronary artery or a tumor arterial supply. This also allows the application of interstitial, implanted radiotherapy while minimizing the exposure of the operator to radiation that is sometimes necessary when using other currently available methods of providing local radiotherapy.

Polymers

Polymers for forming the depot must be biodegradable, i.e., must dissolve into small molecules which can be removed by normal metabolic functions and/or excretion, under the conditions found at the site of application of the depot. In one aspect, the polymers may be slowly soluble under body conditions, for example, certain poloxamers, such as Pluronic™ F-68 (a polyethylene glycol-polyethylene oxide block copolymer marketed by BASF), which gel at body temperature and slowly dissolve over several days. In another aspect, the fluidity of the polymers is altered using temperature. For example, polymers can be melted by heating or by cooling (e.g., with Pluronics™), and applied to the site, where the polymer will re-solidify. Depot formation can also be caused by other known means of coacervation, such as complexation of polymers with ions (e.g., alginate with calcium), direct coacervation of polymers (e.g., polyglutamic acid with polylysine), and exsolvation of polymers by diffusional removal of non-water solvent molecules.

Degradable linkages in the polymers include esters, orthocarbonates, anhydrides, amides and peptides, acetals, phosphazene linkages, and Schiff base adducts. Examples of groups forming suitable ester linkages include hydroxy acids, such as lactic, 10 glycolic, hydroxybutyric, valerolactic and hydroxycaproic. Examples of anhydride-forming groups include oxalic, malonic, succinic, glutaric, adipic, suberic, azelaic sebacic, maleic, fumaric and aspartic. Examples of carbonate-forming compounds include trimethylene carbonate.

In another aspect, the polymers may be crosslinkable in situ. Crosslinking may be by any suitable chemical means. If chemically crosslinked, at least one of the polymer and the linkage formed must be biodegradable. Examples of biodegradable linkages include Schiff bases, anhydrides, disulfides, and acetals. Examples of other linkages, not necessarily biodegradable, include epoxy (oxirane) groups, urethanes, ester, ethers, amides, and sulfones. Linkages involving carbon-carbon double bonds may be formed by a variety of means, including the polymerization of ethylenically-unsaturated groups. These may include (meth) acryl, vinyl, allyl, styryl, cinnamoyl, and alkenyl groups. Such reactions can be initiated by thermal, chemical, radiative or photochemical means. It is known that most chemically crosslinkable groups and molecules will tend to crosslink in the presence of radioactive materials, and are preferably mixed with radioactive materials just before application.

In another aspect, the biodegradable polymer is dissolved in a solvent other than water (an "organic" solvent, broadly construed to include any biocompatible non-aqueous solvent) and deposited at the site, and precipitated as the organic solvent diffuses away from the site, forming a depot. The organic solvent must not cause undue damage to the tissue at the site. This will vary, depending on the tissue and on the condition to be treated. In many applications, ethanol, isopropanol, mineral oil, vegetable oil, and liquid silicones may be suitable.

The biodegradable polymer, and any solvent or adjuvant included in the composition, must further be sufficiently biocompatible for the purposes of the therapy. A biocompatible material is one which arouses little or no tissue reaction to its implantation, and where any reaction is of limited extent and duration. The extent of irritation which is tolerable, or which will be elicited, depends on the site of application. For example, many polymers are minimally irritating on the skin, or within the digestive tract, while only a few polymers are acceptable in the peritoneum. Many materials of high biocompatibllity (minimally irritating) are non-ionic and, after application, contain few reactive or potentially reactive groups. Preferred examples of such materials are poly(alkylene oxides), such as polyethylene glycols, poloxamers, meroxapols and the like.

The depot formed by local deposition of an appropriate biodegradable polymer, normally in combination with the radioactive material at the time of deposition, will be structured to release the radioactive material in a known and predictable manner during biodegradation of the depot. The combined effects of radioactive decay and of controlled release will determine the total energy deposited into the target tissue. Numerous means are known for controlling the release rate of a material from a depot. These include diffusion of the material through a solid polymer; diffusion of the material through pores in a polymer, or in a gel formed from the polymer; burst release of a material on rupture of a compartment; exposure of material to the environment due to erosion of the polymer; slow dissolution of material from a solid form which is maintained in place by the polymer; release of diffusional restrictions on a material by degradation of a solid polymer, a polymeric coating or a gel; release of a material from a degradable linkage to a polymer, or to a carrier material contained in or on a polymer; and de-binding of a reversible association between a material and a polymer, or a carrier material contained in or on a polymer. Combinations of such means may be used to obtain an optimal release profile. For example, a small radiolabelled molecule may be embedded in a degradable microsphere, from which it is slowly released by a combination of diffusion and degradation of the microspheres. The microspheres in turn are restrained at the site of therapy by a polymeric gel formed in situ, which itself provides minimal diffusion barriers and further gradually degrades. Selection of the relative degradation rates of the gel and of the microspheres will influence the total radiation dose administered to the site of therapy. As used herein, microspheres includes microparticles, microcapsules, liposomes, lipid particles, and other formulations of similar size and function.

Radioactive Materials

Any radioactive material may be used. Standard radionuclides which have been used for local radiotherapy may be used, such as radionuclides of iodine, iridium, radium, cesium, yttrium or other elements.

Preferred radioisotopes are those which have a particle range in tissue which is concordant with the thickness of the layer of tissue to be treated. Information on particle ranges is readily available. For example, it is known that about 90% of the energy from a $^{14}C$ (carbon-14) source will be absorbed in about the first 70 microns of tissue, and similar distances will be found for sulfur-35 and phosphorous-33, since their emitted particles are of the same kind as $^{14}C$ (beta particles) and of similar energies. More energetic beta particles would have a longer range, such as those of phosphorous-32, which has a maximum range of about a centimeter and thus can be used to treat thicker tumors, or blood vessels having multi-millimeter thick medial layers. Very high energy emissions, whether of beta particles or of other forms, are generally less preferred because their emissions may exit from the body, thereby causing shielding problems.

The radioisotope must be administered in a pharmaceutically acceptable form. The form must be biocompatible, as described above. The form must also be capable of remaining at the site of application for a controlled length of time, in combination with a means for control of local delivery. For example, the radioisotope could be in the form of an element, an inorganic compound, an organic compound, or attached to a larger molecule, such as a polymer. In the last case, incorporation could be into a backbone group; as a side group, preferably covalently bonded; or as a ligand, bound to a suitable binding group on the polymer. A binding group could be a non-biological binding group, such as a chelator for metal ions; or a biological group for binding, such as avidin for biotin. Likewise, the polymer could be biological, such as a protein, a polysaccharide or a nucleic acid; or it could be synthetic, such as a polyalkylene glycol or a poly(meth)acrylate.

Immobilization of Ions in a Gel

Radioactive ions can be directly immobilized in a gel. In one embodiment, they may be locally converted to a low-solubility salt form, for example by precipitation with an appropriate salt, e.g., as calcium phosphate, or as a ligand on a polymer, or as a cofactor bound to a biological molecule.

In a preferred embodiment, radioactive ions are immobilized in a gel by chelation. A chelator can be covalently immobilized in a gel. The covalently linked chelator ('host') in turn can immobilize the metallic ion ('guest').

Polymerizable macromers or small molecules can be synthesized bearing an appropriate chelator connected to the backbone. An example of a suitable molecule would be one which has one end(s) of the central backbone (e.g., a polyalkylene oxide, such as polyethylene glycol (PEG) or polypropylene oxide/polyethylene oxide (PPO/PEO)) bearing a chelator, optionally attached through a spacer group such as a hydroxyacid. The other end(s) of the PEG backbone would carry a polymerizable bond, with or without spacer groups. This requires a backbone having two or more functionalizable ends. The presence of the backbone is optional; a chelating group could be directly coupled to a reactive group, such as an acryl, allyl or vinyl group, which would participate in the formation of a gel.

An example of a chelator ('host') is the polyazamacrocycle cyclam 1,4,8,11-tetra azacyclo tetradecane which is know to form thermodynamically and kinetically stable complexes with Tc-99m ('guest'), a metal ion used for medical applications.

An example of a guest is technetium-99m, a γ-emitter for clinical applications, which emits only γ-radiation, has a low radiation energy and a short half-life of only 6 hrs. Tc-99m can be used for monitoring physiological changes using scintigraphy, a highly sensitive γ-radiation-based technique used in most hospitals.

These chelator-bearing macromonomers can be delivered as solutions and 'gelled' in the target site using polymerizable crosslinkers (e.g., PEG with acrylate endgroups linked to the PEG by biodegradable spacers)). The degradation and other physical property of the resulting hydrogel can be tailored to desired specifications.

The significance of such a gel is that:

1. Such hydrogels can be formed in situ and can bear a γ-emitter or other medically useful isotope for various medical applications.

2. Since databases for various chelators are available from literature, it is straightforward to find an appropriate chelator to selectively immobilize a particular metal ion within a hydrogel.

3. Other possible applications of the concept include localized delivery or immobilization of medically useful nuclides, localized delivery of physiologically beneficial (and therapeutic) metal ions or other charged species.

Medical Applications

Applications of this technology include the local treatment of tumors, cancer, and other unwanted growths (e.g., atheromae, papillae); inhibition of scarring or healing to prevent excessive scar formation or keloid formation; preservation of surgically-created conduits, for example inhibition of healing over of the sclera following a filtration procedure for glaucoma; prevention of fibrosis and of capsule formation; and prevention of restenosis following angioplasty.

Methods of Application

The local depot can be placed at the site to be treated by any of several methods. For external application, a preformed depot can be applied and secured by appropriate adhesives. An external application would also require appropriate means for prevention of migration of the radioactive material. For internal applications, the depot-forming polymer, preferably in combination with the radioactive material and any required excipients, accessory materials, and drug delivery means, is typically administered in a fluent form to the site of application by a delivery device, and caused or allowed to solidify at the site. Delivery devices can include percutaneous means such as catheters, cannulae, and needles; or means applied through natural or surgically created openings or through temporary openings, such as those created by trocars, using syringes, brushes, pads, or brushes. Similar means are used to apply any stimuli required to form the depot from the fluid polymer material. For example, light may be brought to a remote site via an optical fiber, or a device similar to a laparoscope, to cause polymerization in a depot, or a chemical could be applied by means similar to those used for the depot-forming mixture.

Dose Control

The method provides three ways of controlling the total dose delivered to a site, while simultaneously controlling exposure to other areas of the body. First, the total amount of isotope can be varied. Second, the half-life of the isotope can be selected; this provides an upper limit of the applied dose. Third, the lifetime of the radioisotope in the local delivery depot can be controlled.

For example, if the radioisotope is a macromolecule, then the depot could be a gel, and the rate of release of the macromolecule from the gel can be controlled by making the gel sufficiently dense so that the macromolecule is released only as the gel degrades. Such gels are known; for example, the gels described by U.S. Pat. No. 5,410,016 to Hubbell et al. are suitable.

If the radioisotope is a small molecule, rather than a macromolecule, its rate of release can be controlled by embedding it in a solid bioerodable material, such as polylactide, polycaprolactone, a polyanhydride, or a polymerized biomaterial, such as protein. Then the small molecule is released by a combination of diffusion through the material, and erosion of the material, each of which is adjustable.

Alternatively, the rate of release of a radioisotope may be regulated by selecting the strength of interaction of the molecule with its environment. For example, if both the molecule and the depot are relatively hydrophobic, then the molecule will diffuse out of the depot relatively slowly. If it is not practical to make the depot hydrophobic, then the molecule can be included in more hydrophobic microparticles, such as polymeric microparticles, liposomes, emulsions, etc., which in turn are embedded within a hydrophilic depot.

The present invention will be further understood by reference to the following non-limiting examples.

EXAMPLE 1

Immobilization of a Radionuclide in an Interfacially Deposited Gel.

A radionuclide ($^{125}$I or $^{131}$I or other radionuclide) is deposited in an interfacial hydrogel following angioplasty, either coronary or peripheral, or intravascular stent placement, or carotid artery stent, or an arterectomy. The incorporated radionuclide is chosen to provide a total of exposure of at least 1500 cGy to the arterial wall. The delivered dose is adjusted by choosing the amount of incorporated radionuclide and is further controlled by choosing a formulation of hydrogel with a different persistence at the site of deposition. The duration of exposure at the site of deposition can be controlled by adjusting the biodegradable moieties of the hydrogel or by changing the density of crosslink of the polymer at the site.

EXAMPLE 2

Local Radiotherapy From a Polymer

Applied Via Catherization.

Local radiotherapy can be applied to any tumor which is accessible by a vascular catheter. This technique is particularly applicable to either highly vascularized tumors or tumors which have a single dominant arterial vascular supply. This would provide a method for treatment particularly applicable to renal cell carcinoma, hepatoma, sarcomas, cancers of the head and neck, and central nervous system tumors. In this example, radioactive microspheres containing yttrium-90 are incorporated in a hydrogel that is deposited in the artery supplying a tumor. The local tumor volume in the area of deposition is radiated while the microspheres are immobilized at the site of deposition. On degradation of the hydrogel, the microspheres are released and redeposited in the distal microcirculation, where they provide continued radiation treatment. The exposure at the site of an initial deposition can be regulated by controlling the rate of hydrogel degradation, either by adjusting the biodegradable moieties in the hydrogel or the density of crosslinking. The microspheres can be chosen for a longer time of degradation or elimination of greater than 320 hours, when five half-lives of the implanted yttrium-90 have expired and the vast majority of radioactive decay has occurred.

Modifications and variations will be obvious to those skilled in the art from the foregoing detailed description and are intended to come within the scope of the following claims.

We claim:

1. A method for local radiotherapy at a site in a patient, comprising forming a polymeric depot by combining a radioisotope with a biocompatible synthetic polymer that is in a first fluent state;

administering the combination to the site at which local radiotherapy is to be administered; and reducing the fluidity of the polymer at the site to form a biocompatible biodegradable depot that is in a second, less fluent state, wherein the depot is a hydrogel which releases the radioisotope in a controlled manner.

2. The method of claim 1 wherein the polymer is chemically coupled to the radioisotope via a covalent bond.

3. The method of claim 1 wherein the radioisotope is conjugated to the polymer via a chelating agent coupled to the polymer.

4. The method of claim 1 wherein the depot comprises bioerodible polymeric microspheres comprising the radioisotope.

5. The method of claim 4 wherein the microspheres are biodegradable at a different rate than the depot.

6. The method of claim 1 wherein the fluidity of the polymer is reduced by covalently crosslinking the polymeric material.

7. The method of claim 1 wherein the fluidity of the polymer is reduced using a temperature change.

8. The method of claim 1 wherein the fluidity of the polymer is reduced by coacervation.

9. The method of claim 1 wherein the fluidity of the polymer is reduced by exsolvation.

10. The method of claim 1 wherein the radioisotope is converted at the site to a low-solubility salt form.

11. A composition for local radiotherapy, the composition comprising:

a biocompatible synthetic polymer, and a therapeutically effective amount of a radioisotope which is combined with the biocompatible polymer in a first fluent state to form a biocompatible biodegradable polymeric depot, wherein the polymeric depot is formable into a second, less fluent state in situ at a site in a patient, such that the polymeric depot is a hydrogel and releases a therapeutically effective amount of the radioisotope in a controlled manner.

12. The composition of claim 11 wherein the polymer is chemically coupled to the radioisotope via a covalent bond.

13. The composition of claim 11 wherein the polymer is conjugated to the radioisotope via a chelating agent coupled to the polymer.

14. The composition of claim 11 wherein the depot comprises microspheres comprising the radioisotope.

15. The composition of claim 14 wherein the microspheres are biodegradable at a different rate than the depot.

* * * * *